(12) United States Patent
Prokop (10) Patent No.: US 9,160,896 B1
(45) Date of Patent: Oct. 13, 2015

(54) HIGH SPEED EDGE DETECTION

(71) Applicant: The United States of America as represented by the Administrator of the National Aeronautics and Space Administration, Washington, DC (US)

(72) Inventor: Norman F Prokop, South Euclid, OH (US)

(73) Assignee: The United States of America as Represented by the Administrator of National Aeronautics and Space Administration, Washington, DC (US)

( * ) Notice: Subject to any disclaimer, the term of this patent is extended or adjusted under 35 U.S.C. 154(b) by 382 days.

(21) Appl. No.: 13/749,773

(22) Filed: Jan. 25, 2013

Related U.S. Application Data (60) Provisional application No. 61/654,413, filed on Jun. 1, 2012.

(51) Int. Cl.
   H04N 5/14        (2006.01)
(52) U.S. Cl.
   CPC ..................................... *H04N 5/142* (2013.01)
(58) Field of Classification Search
   CPC ........... H04N 5/142; H04N 5/44; H04N 5/46; H04N 5/23212; H04N 9/045
   USPC .......... 348/169, 333, 308, 311, 143, 553, 558
   See application file for complete search history.

(56) References Cited

U.S. PATENT DOCUMENTS

| | | | |
|---|---|---|---|
| 4,519,041 A | 5/1985 | Fant et al. | |
| 4,821,112 A * | 4/1989 | Sakamoto et al. | 348/555 |
| 4,853,970 A | 8/1989 | Ott et al. | |
| 5,604,821 A | 2/1997 | Ranganathan et al. | |
| 6,130,721 A * | 10/2000 | Yoo et al. | 348/558 |
| 6,587,154 B1 * | 7/2003 | Anderson et al. | 348/553 |
| 6,624,849 B1 | 9/2003 | Nomura | |
| 7,038,185 B1 | 5/2006 | Tumblin et al. | |
| 7,606,445 B2 | 10/2009 | Howard | |
| 7,734,112 B1 | 6/2010 | Martel | |
| 8,009,236 B2 * | 8/2011 | Keener et al. | 348/723 |
| 2010/0296703 A1 | 11/2010 | Marti | |

OTHER PUBLICATIONS

Deans, Matthew C., Schneider, Steven J.: "Development and Testing of a methane/Oxygen Catallytic Microtube Ignition System for Rocket Propulsion", American Institute of Aeronautics and Astronautics.

* cited by examiner

*Primary Examiner* — Trang U Tran
(74) *Attorney, Agent, or Firm* — Robert H. Earp, III (57) ABSTRACT

Analog circuits for detecting edges in pixel arrays are disclosed. A comparator may be configured to receive an all pass signal and a low pass signal for a pixel intensity in an array of pixels. A latch may be configured to receive a counter signal and a latching signal from the comparator. The comparator may be configured to send the latching signal to the latch when the all pass signal is below the low pass signal minus an offset. The latch may be configured to hold a last negative edge location when the latching signal is received from the comparator.

13 Claims, 7 Drawing Sheets

FIG. 1

RELATED ART

HIGH SPEED EDGE DETECTION

CROSS REFERENCE TO RELATED APPLICATION

This application claims the benefit of U.S. Provisional Application Ser. No. 61/654,413, filed on Jun. 1, 2012. The subject matter of the earlier filed provisional patent application is herein in its entirety.

ORIGIN OF THE INVENTION

The invention described herein was made by employees of the United States Government and may be manufactured and used by or for the Government for Government purposes without the payment of any royalties thereon or therefore.

The invention described herein was also made in the performance of work under a NASA contract and is subject to the provisions of Section 305 of the National Aeronautics and Space Action of 1958, Public Law 85-568 (72 Stat. 435; 42 U.S.C. 2457).

FIELD

The present invention generally pertains to edge detection, and more specifically, to high speed edge detection that identifies edges in an image.

BACKGROUND

Image processing techniques are employed for various applications. For instance, techniques are used to identify a dark spot in an image generated by a sheet of laser light projected through an airflow and shock of a jet engine intake. A dark spot represents the location of the shock in the airflow.

One method of identifying the location of the dark spot is using edge detection algorithms on the captured image. The dark spot due to the shock appears as two edges within the image. Conventional techniques use high speed cameras and large computers to accomplish the image processing. This results in a large system that cannot be mounted in an engine intake of an aircraft. By using a computer, digital signal processor ("DSP"), or other digital system to perform the image processing in conventional approaches, the speed, size, and power usage of an overall sensing system depends on the processor and supporting hardware. Accordingly, an improved approach may be beneficial.

SUMMARY

Certain embodiments of the present invention may be implemented and provide solutions to the problems and needs in the art that have not yet been fully solved by conventional edge detection systems. For example, in some embodiments, an analog technique is used to perform the image processing with a smaller, simpler, and more reliable circuit.

In one embodiment of the present invention, an analog signal detection apparatus includes a comparator configured to receive an all pass signal and a low pass signal for a pixel intensity in an array of pixels. The apparatus also includes a latch configured to receive a counter signal and a latching signal from the comparator. The comparator is configured to send the latching signal to the latch when the all pass signal is below the low pass signal minus an offset. The latch is configured to hold a last negative edge location when the latching signal is received from the comparator.

In another embodiment of the present invention, an analog signal detection apparatus includes a comparator configured to receive an all pass signal and a low pass signal for a pixel intensity in an array of pixels. The apparatus also includes a latch configured to receive a counter signal and a latching signal from the comparator. The comparator is configured to send the latching signal to the latch when the all pass signal is above the low pass signal plus an offset. The latch is configured to hold a last positive edge location when the latching signal is received from the comparator.

In yet another embodiment of the present invention, a method includes detecting, by a comparator, an edge by determining when an all pass signal is below a low pass signal minus an offset or the all pass signal is above the low pass signal plus the offset. The method also includes sending, by the comparator, a latching signal to a latch when the edge is detected. The method further includes holding, by the latch, a last edge location when the latching signal is received from the comparator.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE EMBODIMENTS

Some embodiments of the present invention pertain to an analog linear image sensor and processing circuit that identifies positive and/or negative edges in a captured image. In some embodiments, the circuit is capable of capturing and processing linear images at over 900 frames per second. The edges may be identified as numeric pixel values within a linear array of pixels. The edge location information may be output from the circuit in a variety of ways in some embodiments using a microcontroller and onboard or external digital interface. Serial data may be included as RS-232/485, USB, Ethernet, CAN BUS, parallel digital data, an analog signal, or any other suitable format. The linear image sensor and circuit may be integrated into a small package and consist of a relatively small number of components in some embodiments.

Certain embodiments were developed to solve the problem of high speed image processing to identify a shock in the airflow of an aircraft engine's intake. However, numerous other applications are possible. For instance, some embodiments may be used for applications including, but not limited to, bar code scanners, digital cameras, part placement, assembly line applications, position monitoring, and lane line tracking for automatic vehicle control.

Figure 1:
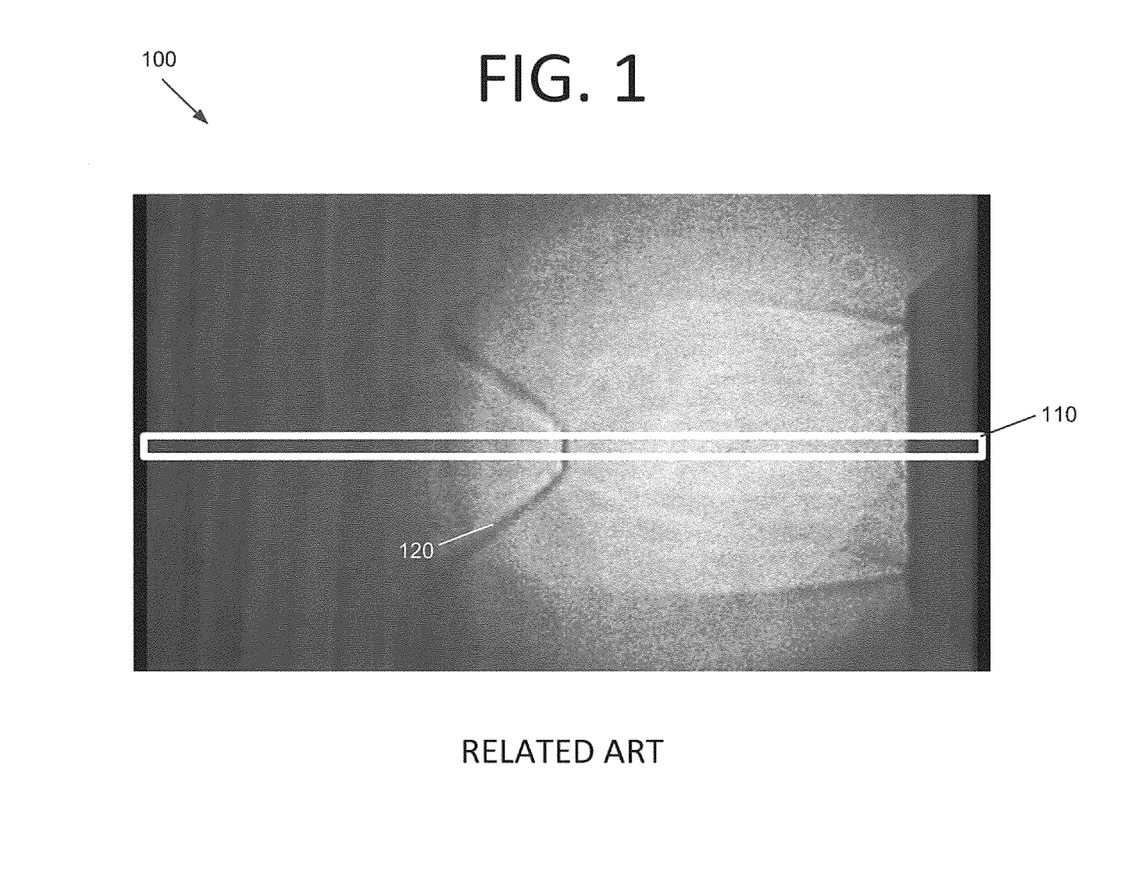
FIG. 1 illustrates a shadowgraph image of engine inlet shock.

In order to better illustrate the operation of some embodiments, it may be useful to consider the example of edge detection for an intake of an aircraft engine. FIG. 1 illustrates a shadowgraph image 100 of engine inlet shock. Box 110 is intended to simulate an outline of one row or line of pixels in the image. However, one of ordinary skill in the art will readily appreciate that box 110 encompasses multiple rows of pixels. The shockwave, or edge, appears as a sideways "V" 120.

Figure 2:
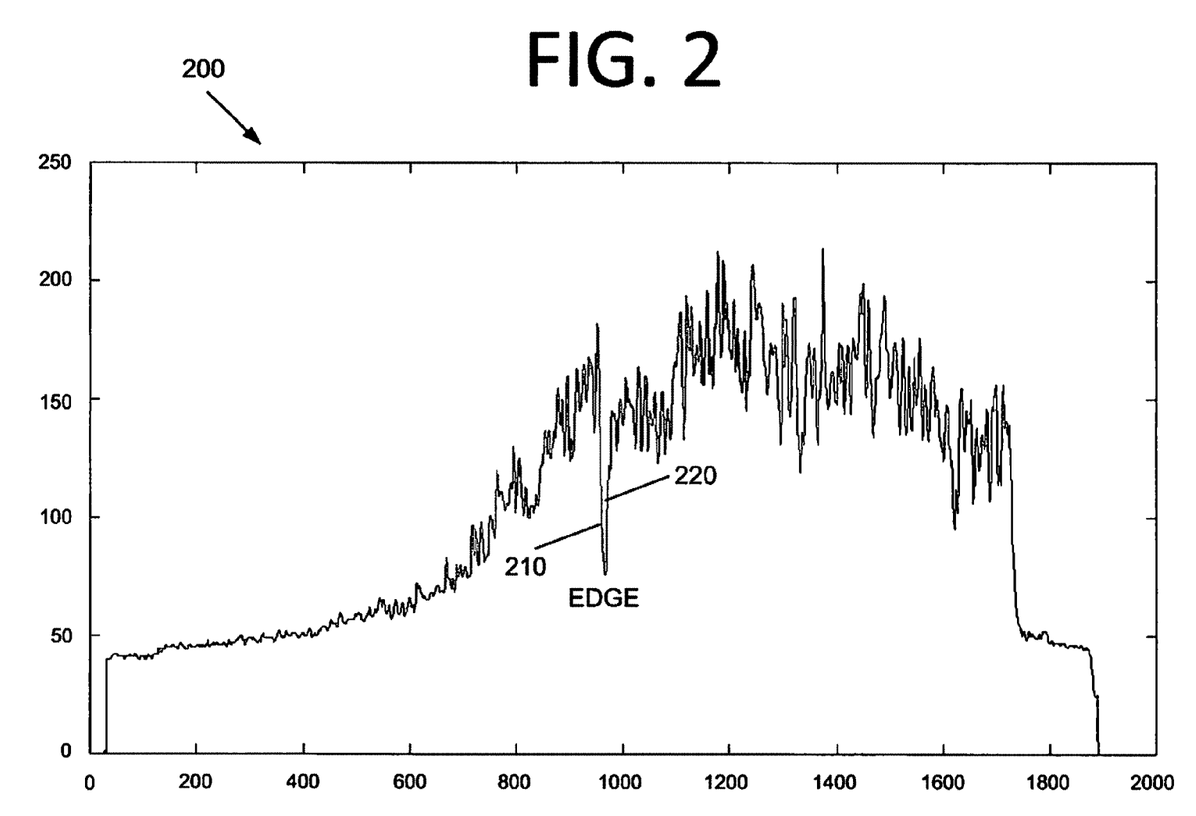
FIG. 2 is a graph illustrating pixel intensity values of the shadowgraph image, according to an embodiment of the present invention.

Some embodiments pertain to a small sensor system that is configured to detect dark spots within a line image. The dark spot shows up as a dip, or negative peak, within the pixel intensity profile of the image (i.e., a small black spot), as is more clearly illustrated in FIG. 2. FIG. 2 is a graph 200 illustrating pixel intensity values of shadowgraph image 100, according to an embodiment of the present invention. Graph 200 plots pixel number along the X axis and pixel intensity in bits as sampled by an 8-bit analog-to-digital converter along the Y axis. The sharp negative peak around pixel 1,000 is V-shaped shock 120 in the middle of shadowgraph 100. The shock, or negative peak, consists of two edges: a negative, or falling, edge 210 and a positive, or rising, edge 220. In machine vision terminology, this "shock shadow" can also be described as a negative going edge followed by a positive going edge.

Figure 3:
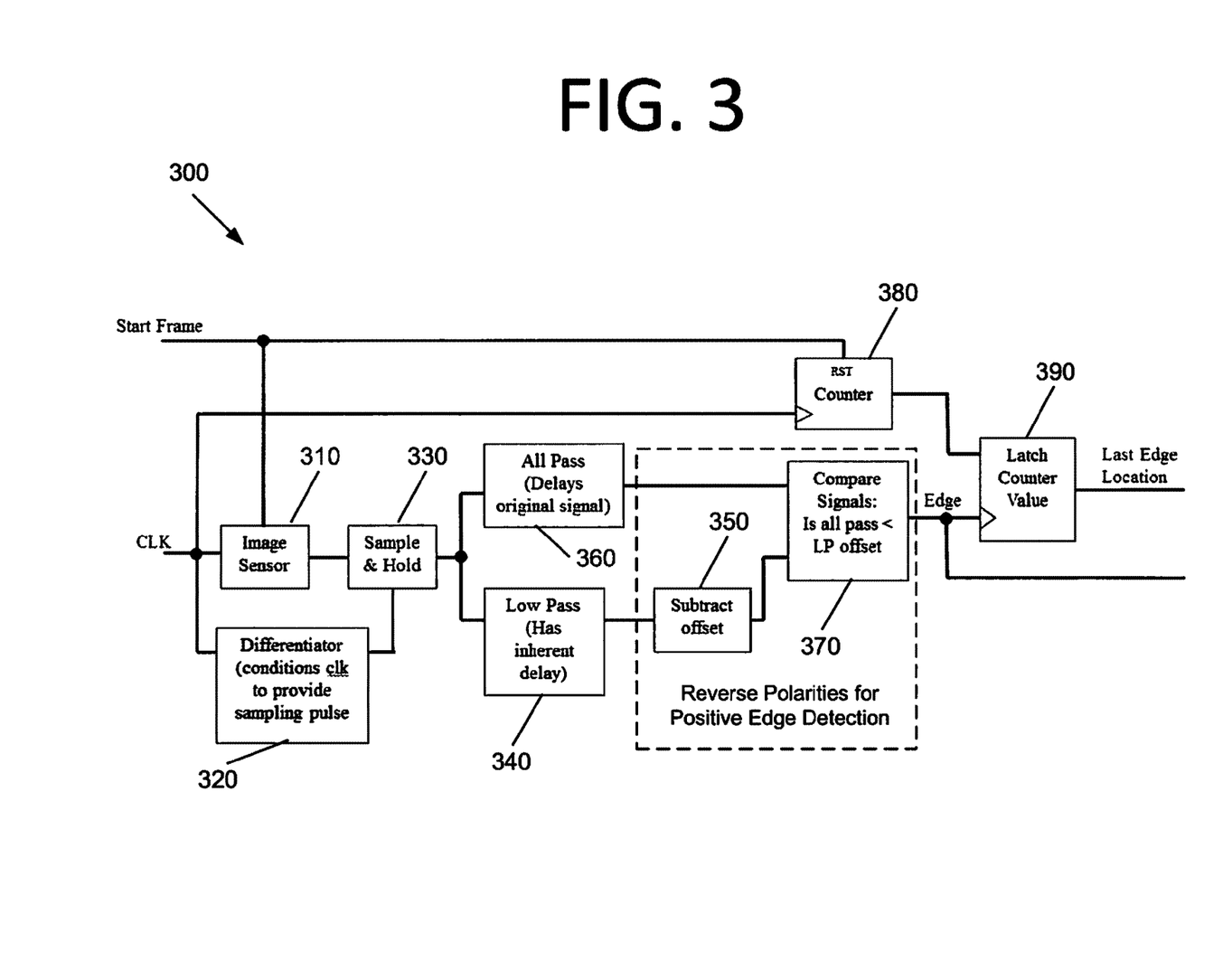
FIG. 3 is a circuit diagram illustrating an analog edge detecting circuit, according to an embodiment of the present invention.

Some embodiments include a linear image sensor, an analog signal processing circuit, and a digital circuit that provide a numerical digital output of the shock or negative edge location. FIG. 3 is a circuit diagram 300 illustrating an analog edge detecting circuit, according to an embodiment of the present invention. Linear image sensor 310 provides an analog voltage for each individual pixel within its array of pixels. To clock the pixels out of the array, a clock signal CLK is provided to the array, and in some embodiments, a microcontroller (not shown) provides this clock signal. A differentiator 320 conditions the CLK signal to provide a sampling pulse. More specifically, differentiator 320 turns the rising edge of the CLK square wave into a short duration pulse for sample and hold 330.

This sampling pulse is then timed to coincide with the analog output voltage from the pixel array. Differentiator 320 may include a capacitor followed by a diode and a comparator circuit with positive feedback hysteresis. The diode allows only the rising clock edge to generate a sampling pulse, bypassing the falling edge. Sample and hold 330 may then reconstruct the individual pixel voltages into a continuous time analog voltage signal which can be input to the two filter networks discussed below.

As the discrete voltages for each pixel are clocked out of linear image sensor 310, the discrete voltages are sampled and held somewhat constant by sample and hold 330 to make a continuous image signal from the discrete pixel voltages. The sample and hold functionality can be accomplished, for example, with a discrete sample and hold integrated circuit, or constructed from an operation amplifier, a high speed switch (or a transistor), and a capacitor. Sample and hold 330 also receives a signal from differentiator 320. The continuous image signal is then operated on using analog signal processing techniques. More specifically, the continuous image signal is applied to two filter networks. The first is an all pass filter 360 that delays the original signal by a constant group delay. The second filter network is a low pass filter 340 that has an inherent delay. Low pass filter 340 filters out high frequency components of the signal and delays the signal by a similar delay to all pass filter 360. A constant offset voltage is then subtracted from the low pass signal by an operational amplifier circuit configured as a difference amplifier 350. This offset voltage provides the sensitivity of the circuit to the depth of the negative going edges.

The outputs of the two filter networks are then compared using a high speed comparator circuit with hysteresis 370. If the all pass signal falls below the low pass signal, then a negative edge is present at that moment and comparator 370 provides a latching signal. In order to perform positive edge detection, the polarities of 350 and 370 are simply reversed. More specifically, the offset is added at 350 and comparator 370 checks whether the all pass signal is greater than the low pass offset.

To effectively determine the location of the pixel at which the negative edge occurred, the pixels are counted using the image sensor clocking signal to drive a counter 380. Counter 380 counts pixels and is reset to zero at the start of a frame (i.e., line). The latch signal from comparator 370 is used as an input to latch the counter circuit value by latch 390, which then holds a digital representation of the numerical value of the edge or shock position (i.e., a pixel number). Latch 390 is triggered by the output of comparator 370 when an edge is present. The output of this processing is the last edge location.

In some embodiments, by processing images in continuous time, images never need to be captured, and the processing can be done in real time. Each of the pixel values is essentially captured by sample and hold 330. Traditional approaches to edge detection to require image capture, then digital processing. Some embodiments of the present invention do not require image capture. Such an approach may also be applied to a captured image if it is converted to an analog continuous time signal with the use of a digital-to-analog converter in the place of image sensor 310.

Figure 4:
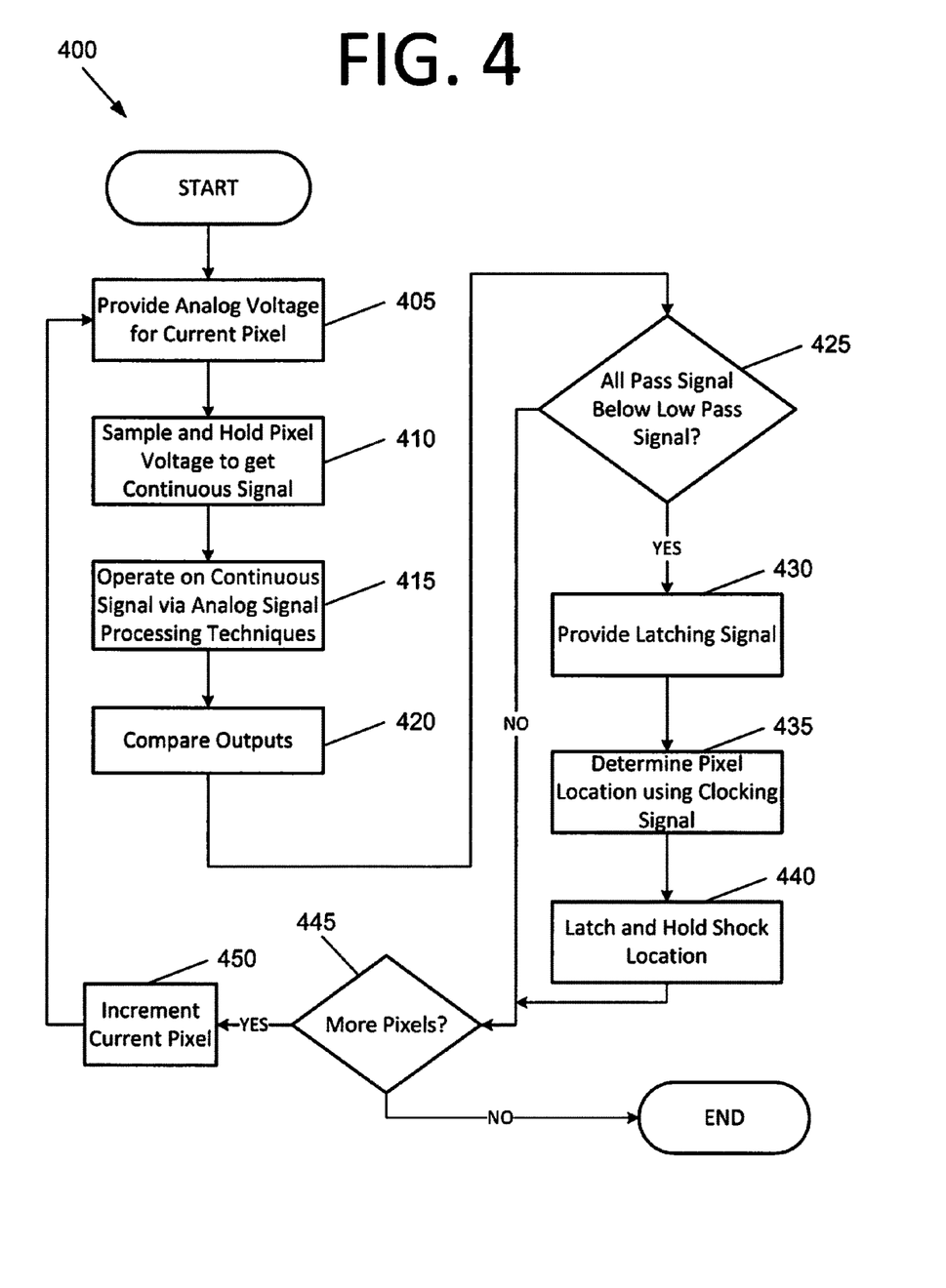
FIG. 4 is a flowchart illustrating a method for analog edge detection, according to an embodiment of the present invention.

FIG. 4 is a flowchart 400 illustrating a method for analog edge detection, according to an embodiment of the present invention. The method begins with providing an analog voltage for the current pixel in a pixel array at 405, beginning with the first pixel to be processed in a pixel array. To clock the pixels out of the array, a clock signal is provided. As the discrete voltage for the current pixel is clocked out, the discrete voltage is sampled and held somewhat constant at 410 to make a continuous image signal from the discrete pixel voltage.

This continuous image signal is then operated on using analog signal processing techniques at 415. This may include applying the continuous image signal to two filter networks. The first filter network may be an all pass filter network that delays the original signal by a constant group delay. The second filter network may be a low pass (and delay) filter network that filters out high frequency components of the signal and delays the signal by a similar delay to the all pass filter network, and then subtracts a constant offset voltage from the low pass signal.

The outputs of the two filter networks are then compared at 420 using, for example, a high speed comparator. For each pixel, if the all pass signal falls below the low pass signal at 425, then a negative edge is present at that moment and the comparator provides a latching signal at 430. The pixel location at which the negative edge occurred is then determined at 435. To effectively determine the location of the pixel at which the negative edge occurred, the pixels are counted using the image sensor clocking signal to drive a counter circuit. The latch signal from the comparator is latched and the shock location is held at 440. This holds a digital representation of the numerical value of the edge or shock position.

Once step 440 is completed, or if the all pass signal is above the low pass signal at 425, the next step is checking whether there are more pixels to process. If there are more pixels in the frame at 445, the current pixel is incremented at 450 and the method returns to step 405. If there are no more pixels to process, the method ends.

Figure 5:
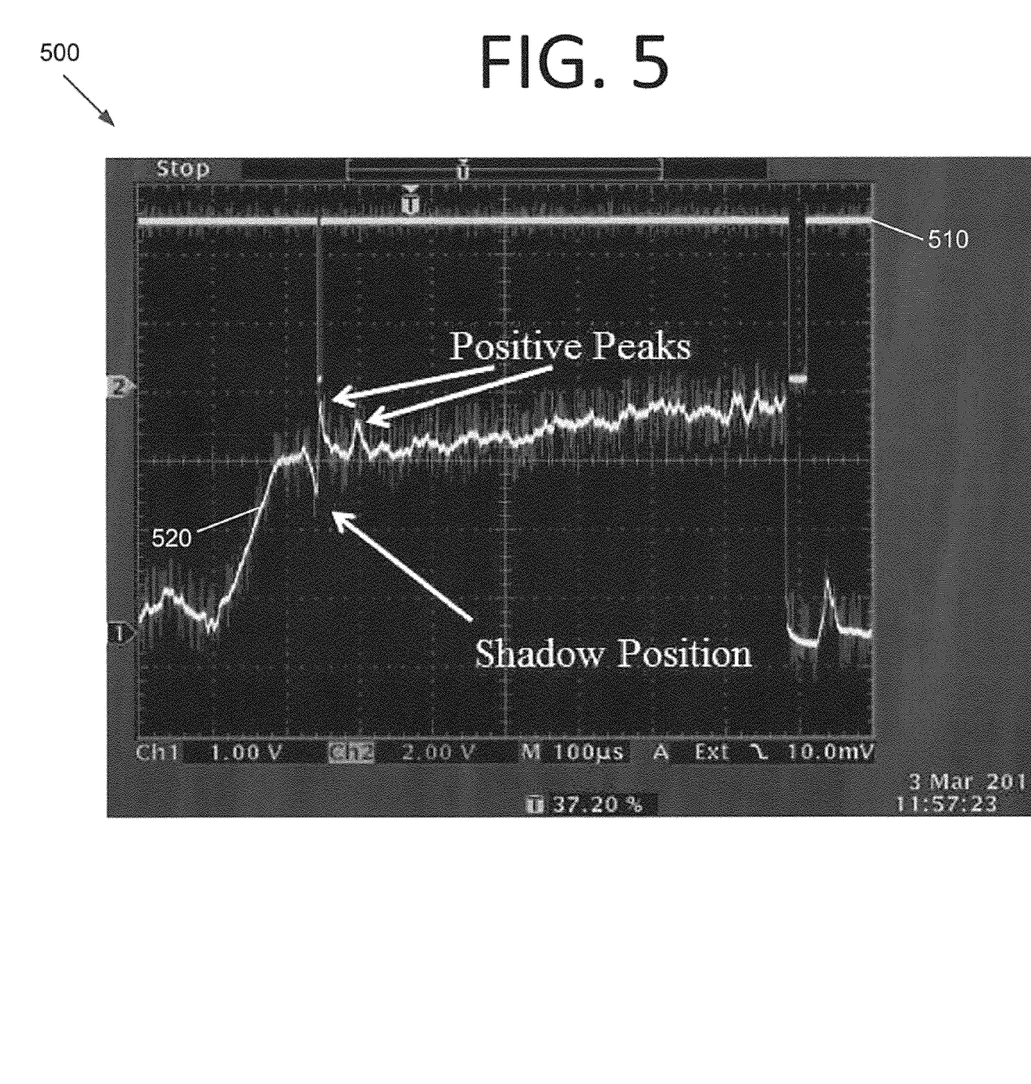
FIG. 5 is a graph illustrating an oscilloscope view of analog edge detection circuit output, according to an embodiment of the present invention.

FIG. 5 is a graph 500 illustrating an oscilloscope view of analog edge detection circuit output, according to an embodiment of the present invention. Upper trace 510 shows output of a comparator, such as comparator 370 of FIG. 3, identifying shock location. Lower trace 520 shows output of a sample and hold analog signal of the image, such as that provided by sample and hold 330 of FIG. 3. This signal is analogous to the pixel intensities, but is not discrete in nature.

Figure 6:
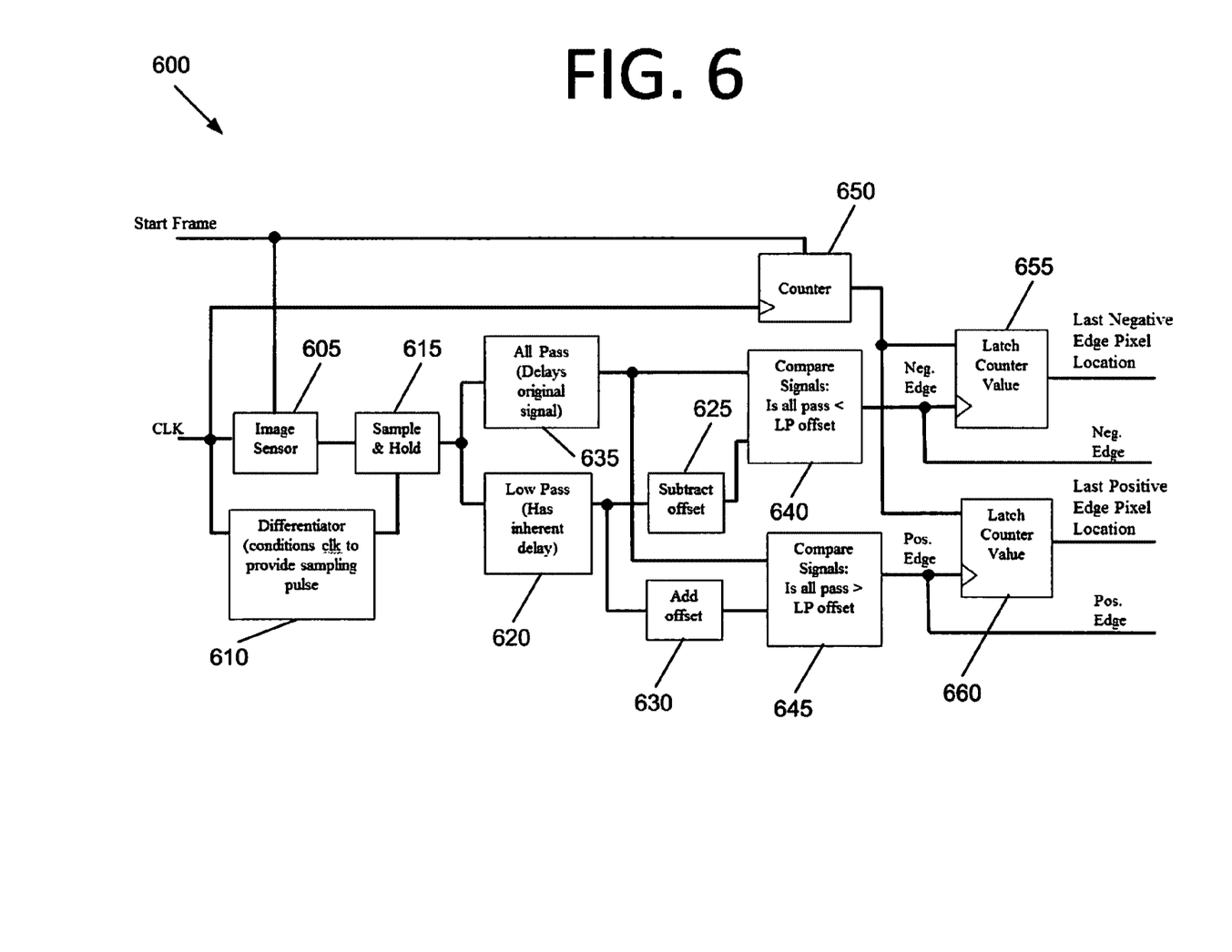
FIG. 6 is a circuit diagram illustrating an analog edge detecting circuit, according to an embodiment of the present invention.

FIG. 6 is a circuit diagram 600 illustrating an analog edge detecting circuit, according to an embodiment of the present invention. Unlike FIG. 3, this circuit is configured to detect both positive and negative edges. Linear image sensor 605 provides an analog voltage for each individual pixel within its array of pixels. To clock the pixels out of the array, a clock signal CLK is provided to the array. A differentiator 610 conditions the CLK signal to provide a sampling pulse by turning the CLK square wave into a short duration pulse.

As the discrete voltages for each pixel are clocked out of linear image sensor 605, the discrete voltages are sampled and held somewhat constant by sample and hold 615 to make a continuous image signal from the discrete pixel voltages. Sample and hold 615 also receives a signal from differentiator 610. The continuous image signal is then operated on using analog signal processing techniques. More specifically, the continuous image signal is applied to two filter networks. The first is an all pass filter 635 that delays the original signal by a constant group delay. The second filter network is a low pass filter 620 that has an inherent delay. Low pass filter 620 filters out high frequency components of the signal and delays the signal by a similar delay to all pass filter 635. A constant offset voltage is then subtracted from the low pass signal by a difference amplifier circuit 625 and a constant offset voltage is added to the low pass signal by a summing amplifier circuit 630. These offset voltages provide the sensitivity of the circuit to the depth of the negative going edges and positive going edges, respectively, and can be held constant or be time-varying.

The outputs of the two filter networks are then compared using high speed comparators 640 and 645. If the all pass signal falls below the low pass signal in comparator 640, then a negative edge is present at that moment and comparator 640 provides a latching signal. If the all pass signal rises above the low pass signal in comparator 645, then a positive edge is present at that moment and comparator 645 provides a latching signal.

To effectively determine the location of the pixel at which the negative or positive edge occurred, the pixels are counted using the image sensor clocking signal to drive a counter 650. Counter 650 counts pixels and is reset to zero at the start of a frame (i.e., line). The latch signals from comparators 640 and 645 are used as an input to latch the counter circuit value by latches 655 and 660, respectively, which then hold a digital representation of the numerical value of the positive and negative edge or shock positions, respectively.

Figure 7:
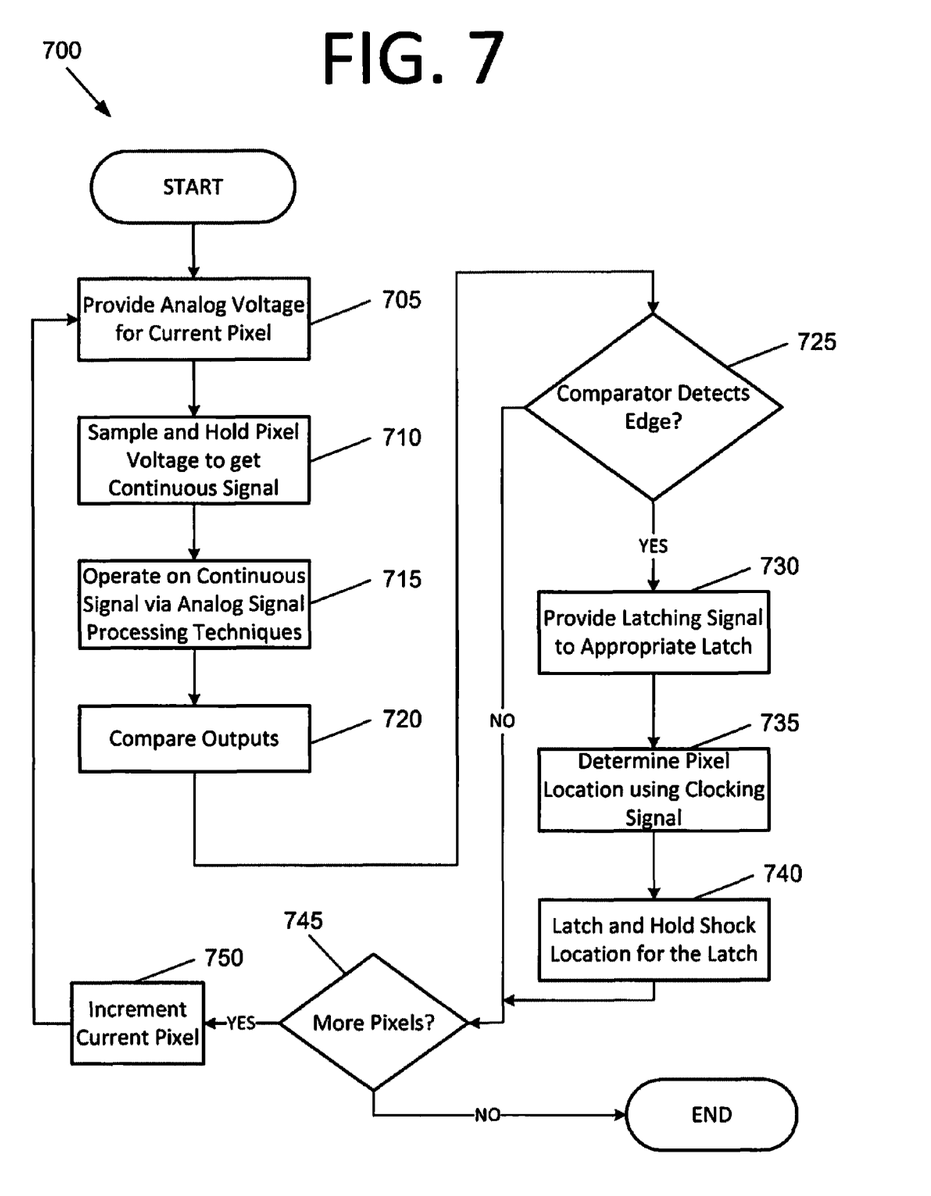
FIG. 7 is a flowchart illustrating a method for analog edge detection, according to an embodiment of the present invention.

FIG. 7 is a flowchart 700 illustrating a method for analog edge detection, according to an embodiment of the present invention. Unlike the method of FIG. 4, the method of FIG. 7 detects both positive and negative edges. The method begins with providing an analog voltage for the current pixel in a pixel array at 705, beginning with the first pixel to be processed in a pixel array. To clock the pixels out of the array, a clock signal is provided. As the discrete voltage for the current pixel is clocked out, the discrete voltage is sampled and held somewhat constant at 710 to make a continuous image signal from the discrete pixel voltage.

This continuous image signal is then operated on using analog signal processing techniques at 715. This may include applying the continuous image signal to two filter networks. The first filter network may be an all pass filter network that delays the original signal by a constant group delay. The second filter network may be a low pass (and delay) filter network that filters out high frequency components of the signal and delays the signal by a similar delay to the all pass filter network, and then subtracts a constant offset voltage from the low pass signal to detect negative edges, and adds a constant offset to the low pass signal to detect positive edges.

The outputs of the two filter networks are then compared at 720 using, for example, two high speed comparators. For each pixel, if the all pass signal falls below the low pass signal for a negative edge detecting comparator or rises above the low pass signal for a positive edge detecting comparator at 725, then a negative or positive edge is present at that moment and the appropriate comparator provides a latching signal to a respective latch at 730. The pixel location at which the edge occurred is then determined at 735. To effectively determine the location of the pixel at which the edge occurred, the pixels are counted using the image sensor clocking signal to drive a counter circuit. The latch signal from the appropriate comparator is latched by the respective latch, and the shock location is held at 740. This holds a digital representation of the numerical value of the edge or shock position.

Once step 740 is completed, or if no edge is detected at 725, the next step is checking whether there are more pixels to process. If there are more pixels in the frame at 745, the current pixel is incremented at 750 and the method returns to step 705. If there are no more pixels to process, the method ends.

It will be readily understood that the components of various embodiments of the present invention, as generally described and illustrated in the figures herein, may be arranged and designed in a wide variety of different configurations. Thus, the detailed description of the embodiments of the systems, apparatuses, methods, and computer programs of the present invention, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. An analog signal detection apparatus, comprising:
a comparator configured to receive an all pass signal and a low pass signal for a pixel intensity in an array of pixels; and
a latch configured to receive a counter signal and a latching signal from the comparator, wherein
the comparator is configured to send the latching signal to the latch when the all pass signal is below the low pass signal minus an offset, and
the latch is configured to hold a last negative edge location when the latching signal is received from the comparator.

2. The analog signal detection apparatus of claim 1, further comprising:
a linear image sensor configured to provide an analog voltage for each pixel in an array of pixels.

3. The analog signal detection apparatus of claim 2, further comprising:
a differentiator configured to convert a clock signal square wave into a short duration pulse; and
a sample and hold component configured to make a continuous image signal from discrete pixel voltages received from the linear image sensor.

4. The analog signal detection apparatus of claim 3, further comprising:
an all pass filter configured to delay the continuous image signal by a constant group delay.

5. The analog signal detection apparatus of claim 1, further comprising:
an offset component configured to determine the offset by subtracting a constant offset voltage from the low pass signal, wherein the offset voltage is configured to provide a predetermined sensitivity to a depth of negative going edges.

6. The analog signal detection apparatus of claim 1, further comprising:
a counter configured to use a clocking signal to determine locations of individual pixels in the array of pixels.

7. The analog signal detection apparatus of claim 1, further comprising:
a second comparator configured to receive the all pass signal and the low pass signal; and
a second latch configured to receive the counter signal and a latching signal from the second comparator, wherein
the second comparator is configured to send the latching signal to the second latch when the all pass signal is above the low pass signal plus the offset, and
the second latch is configured to hold a last positive edge location when the latching signal is received from the second comparator.

8. An analog signal detection apparatus, comprising:
a comparator configured to receive an all pass signal and a low pass signal for a pixel intensity in an array of pixels; and
a latch configured to receive a counter signal and a latching signal from the comparator, wherein
the comparator is configured to send the latching signal to the latch when the all pass signal is above the low pass signal plus an offset,
the latch is configured to hold a last positive edge location when the latching signal is received from the comparator;
a second comparator configured to receive the all pass signal and the low pass signal; and
a second latch configured to receive the counter signal and a latching signal from the second comparator, wherein
the second comparator is configured to send the latching signal to the second latch when the all pass signal is below the low pass signal minus the offset, and
the second latch is configured to hold a last negative edge location when the latching signal is received from the second comparator.

9. The analog signal detection apparatus of claim 8, further comprising:
a linear image sensor configured to provide an analog voltage for each pixel in an array of pixels.

10. The analog signal detection apparatus of claim 9, further comprising:
a differentiator configured to convert a clock signal square wave into a short duration pulse; and
a sample and hold component configured to make a continuous image signal from discrete pixel voltages received from the linear image sensor.

11. The analog signal detection apparatus of claim 10, further comprising:
an all pass filter configured to delay the continuous image signal by a constant group delay.

12. The analog signal detection apparatus of claim 8, further comprising:
an offset component configured to determine the offset by adding a constant offset voltage to the low pass signal, wherein the offset voltage is configured to provide a predetermined sensitivity to a depth of positive going edges.

13. The analog signal detection apparatus of claim 8, further comprising:

a counter configured to use a clocking signal to determine locations of individual pixels in the array of pixels.

* * * * *